United States Patent [19]

Stoll

[11] Patent Number: 5,075,046

[45] Date of Patent: Dec. 24, 1991

[54] PROCESS FOR THE PRODUCTION OF VICINALLY DIACYLOXY-SUBSTITUTED

[75] Inventor: Gerhard Stoll, Korschenbroich, Fed. Rep. of Germany

[73] Assignee: Henkel Kommanditgesellschaft auf Aktien, Duesseldorf-Holthausen, Fed. Rep. of Germany

[21] Appl. No.: 349,468

[22] Filed: May 8, 1989

[30] Foreign Application Priority Data

May 9, 1988 [DE] Fed. Rep. of Germany ....... 3815826

[51] Int. Cl.$^5$ ............................................... C09F 5/08
[52] U.S. Cl. .................................................. 560/410.6
[58] Field of Search ...................................... 260/410.6

[56] References Cited

U.S. PATENT DOCUMENTS 2,485,160 10/1949 Niederhauser et al. .......... 260/410.6
3,993,605 11/1976 Scholz-Weigl et al. .......... 260/410.6

FOREIGN PATENT DOCUMENTS 3002861 1/1980 Fed. Rep. of Germany ... 200/410.6

OTHER PUBLICATIONS

American Heritage Dictionary, p. 1347, 2nd College Edition.
Fessenden, Joan S. and Ralph J., Organic Chemistry p. 344.
Marc Loudon, Organic Chemistry, Second Edition, p. 136.
J. Chem. Eng. Data 5, 231 (1960).
Ind. Eng. Chem. 46, 2205 (1954).
J. Chem. Svc. Perkin Trans. I, 1975, 231 to 241.
Liebigs Ann. Chem. 138, 297 (1866).

Primary Examiner—Jose G. Dess
Assistant Examiner—Deborah D. Carr
Attorney, Agent, or Firm—Ernest G. Szoke; Wayne C. Jaeschke; Daniel S. Ortiz

[57] ABSTRACT

Vicinally diacyloxy-substituted compounds of the formulae Ia, Ib, Ic and Id

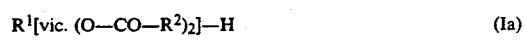

$R^1$[vic. (O—CO—$R^2$)$_2$]—H     (Ia)

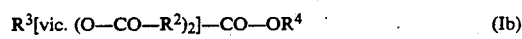

$R^3$[vic. (O—CO—$R^2$)$_2$]—CO—O$R^4$     (Ib)

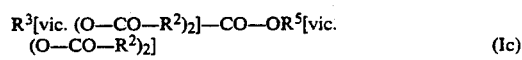

$R^3$[vic. (O—CO—$R^2$)$_2$]—CO—O$R^5$[vic. (O—CO—$R^2$)$_2$]     (Ic)

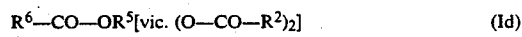

$R^6$—CO—O$R^5$[vic. (O—CO—$R^2$)$_2$]     (Id)

in which
$R^1$ is a trivalent saturated $C_{6-22}$ hydrocarbon radical,
$R^2$ is a $C_{1-3}$ alkyl radical,
$R^3$ is a trivalent saturated $C_{10-21}$ hydrocarbon radical,
$R^4$ is a $C_{1-22}$ alkyl radical,
$R^5$ is a trivalent saturated $C_{16-22}$ hydrocarbon radical, and
$R^6$ is a $C_{1-21}$ alkyl radical, are prepared from the corresponding epoxidized compounds by reaction with $C_{2-4}$ carboxylic anhydrides at elevated temperature in the presence of catalytic quantities of carboxylic acids corresponding to the anhydrides and/or catalytic quantities of sulfuric acid.

7 Claims, No Drawings

PROCESS FOR THE PRODUCTION OF VICINALLY DIACYLOXY-SUBSTITUTED

BACKGROUND OF THE INVENTION

1. Field of the Invention

The invention is a process for the production of vicinally diacyloxy-substituted compounds including diacyloxyalkanes and esters of diacyloxy fatty acids with alkanols and diacyloxy fatty alcohols and of esters of fatty acids with diacyloxy fatty alcohols which correspond to formulae Ia, Ib, Ic and Id below:

$$R^1[\text{vic. }(O-CO-R^2)_2]-H \quad \text{(Ia)}$$

$$R^3[\text{vic. }(O-CO-R^2)_2]-CO-OR^4 \quad \text{(Ib)}$$

$$R^3[\text{vic. }(O-CO-R^2)_2]-CO-OR^5[\text{vic. }(O-CO-R^2)_2] \quad \text{(Ic)}$$

$$R^6-CO-OR^5[\text{vic. }(O-CO-R^2)_2] \quad \text{(Id)}$$

in which
$R^1$ is a trivalent saturated $C_{6\text{-}22}$ hydrocarbon radical,
$R^2$ is a $C_{1\text{-}3}$ alkyl radical,
$R^3$ is a trivalent saturated $C_{10\text{-}21}$ hydrocarbon radical,
$R^4$ is a $C_{1\text{-}22}$ alkyl radical,
$R^5$ is a trivalent saturated $C_{16\text{-}22}$ hydrocarbon radical and
$R^6$ is a $C_{1\text{-}21}$ alkyl radical.

2. Statement of Related Art

Vicinally diacyloxy-substituted compounds are known. Vicinal diacyloxy fatty acid esters have been used inter alia as plasticizers (J. Chem. Eng. Data 5, 231 (1960), as synthetic lubricants (Ind. Eng. Chem. 46, 2205 (1954)) and in foam-regulated cleaning preparations, laundry detergents and dishwashing detergents (DE-C 24 27 125).

There are various known processes for the production of diacyloxy fatty acid esters. For example, vicinal diols may be acylated with the anhydrides of carboxylic acids and/or with carboxylic acid halides, c. Ind. Eng. Chem. 46. The secondary products of the ring opening of epoxides with carboxylic acids, i.e. the (2-hydroxyalkyl)-esters, may also be acylated with anhydrides and/or acid halides, cf. De-C 24 27 125 as cited above and J. Chem. Soc. Perkin Trans. I. 1975, 231 to 241. In addition, vicinal diacyl compounds may be directly produced from the corresponding olefins by oxidative acetylation using Pb(IV) acetate, Tl(III) acetate, Hg(II) acetate, Fe(II) persulfate/acetic acid and Pd(II) acetate. Liebigs Ann. Chem. 138, 297 (1866) reports on the production of vicinal diacetates by reaction of epichlorohydrin with acetic anhydride in a closed loop at 180° C.

BRIEF DESCRIPTION OF THE INVENTION

Other than in the operating examples and claims, or where otherwise indicated, all numbers expressing quantities of ingredients or reaction conditions used herein are to be understood as modified in all instances by the terms "about".

It has now been discovered that vicinally diacyloxy-substituted compounds can be produced by reacting epoxide compounds corresponding to general formulae IIa, IIb, IIc and IId $$R^7(\text{EpO})-H \quad \text{(IIa)}$$

$$R^8(\text{EpO})-CO-OR^4 \quad \text{(IIb)}$$

$$R^8(\text{EpO})-CO-OR^9(\text{EpO}) \quad \text{(IIc)}$$

$$R^6-CO-OR^9(\text{EpO}) \quad \text{(IId)}$$

in which
$R^7(\text{EpO})$ is an epoxidized $C_{6\text{-}22}$ alkenyl radical,
$R^8(\text{EpO})$ is an epoxidized $C_{10\text{-}21}$ alkenyl radical and
$R^9(\text{EpO})$ is an epoxidized $C_{16\text{-}22}$ alkenyl radical
and $R^4$ and $R^6$ are as defined above, with $C_{2\text{-}4}$ carboxylic anhydrides corresponding to formula III $$(R^2-CO-)_2O \quad \text{(III)}$$

in which $R^2$ is as defined above, at elevated temperature in the presence of catalytic quantities of the carboxylic acids $R^2-COOH$, corresponding to the carboxylic anhydrides and/or catalytic quantities of sulfuric acid. The diacyloxy compounds prepared by the process of the invention include diacyloxyalkanes and esters of diacyloxy fatty acids with alkanols and diacyloxy fatty alcohols and of esters of fatty acids with diacyloxy fatty alcohols which correspond to formulae Ia, Ib, Ic and Id below:

$$R^1[\text{vic. }(O-CO-R^2)_2]-H \quad \text{(Ia)}$$

$$R^3[\text{vic. }(O-CO-R^2)_2]-CO-OR^4 \quad \text{(Ib)}$$

$$R^3[\text{vic. }(O-CO-R^2)_2]-CO-OR^5[\text{vic. }(O-CO-R^2)_2] \quad \text{(Ic)}$$

$$R^6-CO-OR^5[\text{vic. }(O-CO-R^2)_2] \quad \text{(Id)}$$

in which
$R^1$ is a trivalent saturated $C_{6\text{-}22}$ hydrocarbon radical,
$R^2$ is a $C_{1\text{-}3}$ alkyl radical,
$R^3$ is a trivalent saturated $C_{10\text{-}21}$ hydrocarbon radical,
$R^4$ is a $C_{1\text{-}22}$ alkyl radical,
$R^5$ is a trivalent saturated $C_{16\text{-}22}$ hydrocarbon radical and
$R^6$ is a $C_{1\text{-}21}$ alkyl radical.

DETAILED DESCRIPTION OF THE INVENTION

The epoxide compounds corresponding to general formulae IIa, IIb, IIc and IId used as starting compounds for the process according to the invention may be prepared
in which
$R^7(\text{EpO})$ is an epoxidized $C_{6\text{-}22}$ alkenyl radical,
$R^8(\text{EpO})$ is an epoxidized $C_{10\text{-}21}$ alkenyl radical and
$R^9(\text{EpO})$ is an epoxidized $C_{16\text{-}22}$ alkenyl radical
and $R^4$ and $R^6$ are as defined above, with $C_{2\text{-}4}$ carboxylic anhydrides corresponding to formula III $$(R^2-CO-)_2O \quad \text{(III)}$$

in which $R^2$ is as defined above, at elevated temperature in the presence of catalytic quantities of the carboxylic acids $R^2-COOH$, corresponding to the carboxylic anhydrides and/or catalytic quantities of sulfuric acid. The diacyloxy compounds prepared by the process of the invention include diacyloxyalkanes and esters of diacyloxy fatty acids with alkanols and diacyloxy fatty alcohols and of esters of fatty acids with diacyloxy fatty alcohols which correspond to formulae Ia, Ib, Ic and Id below:

$$R^1[\text{vic. }(O-CO-R^2)_2]-H \quad \text{(Ia)}$$

$$R^3[\text{vic. } (O-CO-R^2)_2]-CO-OR^4 \quad (Ib)$$

$$R^3[\text{vic. } (O-CO-R^2)_2]-CO-OR^5[\text{vic. } (O-CO-R^2)_2] \quad (Ic)$$

$$R^6-CO-OR^5[\text{vic. } (O-CO-R^2)_2] \quad (Id)$$

in which $R^1$ is a trivalent saturated $C_{6-22}$ hydrocarbon radical,
$R^2$ is a $C_{1-3}$ alkyl radical,
$R^3$ is a trivalent saturated $C_{10-21}$ hydrocarbon radical,
$R^4$ is a $C_{1-22}$ alkyl radical,
$R^5$ is a trivalent saturated $C_{16-22}$ hydrocarbon radical and
$R^6$ is a $C_{1-21}$ alkyl radical.

The epoxide compounds corresponding to general formulae IIa, IIb, IIc and IId used as starting compounds for the process according to the invention may be prepared by standard epoxidation of unsaturated compounds corresponding to general formulae IVa, IVb, IVc and IVd $$R^7-H \quad (IVa)$$

$$R^8-CO-OR^4 \quad (IVb)$$

$$R^8-CO-OR^9 \quad (IVc)$$

$$R^6-CO-OR^9 \quad (IVd)$$

in which $R^4$ and $R^6$ are as defined above and $R^7$ is a $C_{6-22}$ alkenyl radical, $R^8$ is a $C_{10-21}$ alkenyl radical and $R^9$ is a $C_{16-22}$ alkenyl radical.

The alkenes corresponding to formula IVa, which may be linear or branched, are known compounds, typical representatives being hexene, octene, decene, undecene, dodecene, tetradecene, hexadecene, octadecene, eicosene and docosene.

Esters of unsaturated, linear or branched, particularly linear, fatty acids with monohydric $C_{1-22}$ alkanols like methanol, ethanol, n-propanol, n-butanol, n-pentanol, n-hexanol, n-octanol, n-decanol, n-dodecanol, n-tetradecanol, n-hexadecanol, n-octadecanol, n-eicosanol and n-docosanol as well as their branched isomers like 3-methyl butanol (isoamyl alcohol) and 2-ethyl hexanol (isooocatanol) are used as the starting compounds of formula IVb. Unsaturated fatty acids of the formula $R^8$—COOH may be of synthetic origin, for example undecylenic acid, or natural origin, for example palmitoleic, oleic, petroselic, gadoleic and/or erucic acid. Unsaturated fatty acids such as these may be obtained in particular from natural fats and oils, for example from sunflower oil, soybean oil, rapeseed oil and coriander oil; they may also be obtained from animal fats, such as beef tallow and lard. They are generally processed in the form of their technical mixtures to form the fatty acid esters of formula IVb. Accordingly, technical mixtures of the epoxidized fatty acid esters corresponding to formula IVb are preferably used for the process according to the invention. The monohydric alcohol component of the fatty acid esters corresponding to general formula IVb may be derived from methanol, ethanol, n-propanol, i-propanol and butanol, including their isomers.

The starting compounds corresponding to general formula IVc are derived from the fatty acids $R^8$—COOH with the meanings defined above and unsaturated linear or branched, particularly linear, fatty alcohols of synthetic and, in particular, natural origin; typical examples of these fatty alcohols are palmitoleyl, oleyl, elaidinyl, gadoleyl and erucyl alcohol, including the technical mixtures thereof typically encountered in olechemistry.

The starting compounds corresponding to general formula IVd are esters of saturated, linear or branched, particularly linear, $C_{1-22}$ fatty acids with the unsaturated fatty alcohols $R^9$—OH mentioned above. Typical representatives of the fatty acids $R^6$—CO—OH are acetic, propionic, butyric, valeric, caproic, enanthic, caprylic, pelargonic, cparic, hendecanoic, lauric, myristic, palmitic, stearic, arachidic and benhenic acids. The technical mixtures of these fatty acids of synthetic and, in particular, natural origin typically encountered in olechemistry may be used for the higher carboxylic acids of this series ($C_6$ to $C_{22}$).

Depending on the structure of the unsaturated compounds corresponding to general formulae IVb, IVc and IVd, the epoxidation reaction gives compounds which are epoxidized only in the fatty acid part, only in the fatty alcohol part or both in the fatty acid part and in the fatty alcohol part. Technical mixtures of the unsaturated compounds may be prepared from natural raw materials, particularly when, as typical in oleochemistry, they contain fatty acid esters with more than one olefinic double bond in the fatty acid part and/or fatty alcohol part. Typical examples are the corresponding derivatives of linoleic and linolenic acid and linoleyl alcohol and linolenyl alcohol which may be obtained, for example, from linseed oil. With starting compounds such as these, epoxidation and subsequent ring opening by the process according to the invention can result in the formation of mixtures which, in addition to the compounds of formulae Ib to Id also contain certain proportions of compounds in the form of ring-opening products of epoxide compounds containing more than one or more than two epoxide functions. The same applies where technical mixtures of the alkenes IVa are used as starting materials.

A particularly favorable process for the production of the epoxide compounds used as starting compounds in the process according to the invention comprises epoxidation with performic acid formed "in situ", for example in accordance with De-A 30 02 861 and US-C 2,485,160.

In the process according to the invention, the epoxide compounds corresponding to general formulae IIa to IId are reacted with anhydrides of $C_{2-4}$ carboxylic acids, for example with propionic or butyric anhydride, but preferably with acetic anhydride, the reaction being carried out at elevated temperature/atmospheric pressure in the presence of effective quantities of the carboxylic acids corresponding to the anhydrides used and/or sulfuric acid. Preferred quantities for the carboxylic acids used are 0.5 to 15 mol %. Catalytic quantities, more especially 0.1 to 3 mol %, of sulfuric acid may also be added instead of or together with the carboxylic acids. The mol percentages are based on the mols of epoxide functions present in the starting compounds.

In a preferred embodiment of the process of the invention, the reaction is carried out under ambient pressure at the boiling point of the particular reaction mixture. In another preferred embodiment, the reaction is carried out in the absence of solvents, the carboxylic anhydride used being added in excess as solvent. After the reaction, the reaction system is neutralized with anhydrous bases, for example with sodium alcoholate.

Excess or unreacted $C_{2-4}$ carboxylic anhydride is preferably removed by distillation, optionally under reduced pressure. The neutralization products formed during neutralization of the carboxylic acids and/or sulfuric acid used as catalysts are precipitated and may readily be removed by filtration.

The process according to the invention is illustrated by the following Examples in which the quantities shown in mol % for carboxylic acids and/or sulfuric acid are based on mols of epoxide functions present.

EXAMPLES

Example 1

Vicinal Diacetyl Stearic Acid Methyl Ester

6 Mol of an epoxidized oleic acid methyl ester (epoxide oxygen content: 4.61%) were stirred for 4 hours under vigorous reflux with 12 mol acetic anhydride, 10 mol % acetic acid and 1 mol % concentrated sulfuric acid. After neutralization with sodium methylate, the excess acetic anhydride was distilled off; the residue was distilled in a water jet vacuum (approx. 15 torr) up to 120° C. to remove volatile fractions of acetic anhydride. Precipitated salts were removed from the distillation residue by filtration. A brown clear liquid having the following analytical data was obtained: epoxide oxygen content 0.32%, OH value 2.6, saponification value 294.4, acid value 1.1, iodine value 14.7.

Example 2

Vicinal Diacetyl Stearic Acid I-Octyl Ester

1 Mol of an epoxidized oleic acid isooctyl ester (epoxide oxygen content: 3.73%) was stirred under reflux for 6 hours with 2 mol acetic anhydride, 10 mol % acetic acid and 1 mol % concentrated sulfuric acid. After neutralization with sodium methylate, the excess acetic anhydride was distilled off. The reside was distilled in an oil pump vacuum up to 120° C. to remove volatile fractions. The distillation residue was freed from precipitated salts by filtration. A yellow-brown clear liquid having the following analysis was obtained: epoxide oxygen content 0.36%, OH value 1.1, saponification value 232.7 (theoretical 325), acid value 0.6, iodine values 10.0.

The compound obtained showed a pronounced foam-inhibiting effect and, in addition, very good biodegradability.

Example 3

Vicinal Dipropionyl Stearic Acid Isooctyl Ester

1 Mol epoxidized oleic acid isooctyl ester (epoxide oxygen content 3.82%), 2 mol propionic anhydride, 10 mol % propionic acid and 1 mol % concentrated sulfuric acid were reacted for 6 hours at 150° C. as described in Example 2. A product having the following analysis was obtained after the removal of volatile fractions and filtration: epoxide oxygen content 0.20%, OH value 0.6, acid value 1.2, saponification value 240.8, iodine value 8.6.

Example 4

Vicinal Dibutanoyl Stearic Acid Isooctyl Ester

1 Mol epoxidized oleic acid isooctyl ester (epoxide oxygen content 3.82%), 2 mol butyric anhydride, 10 mol % butyric acid and 1.5 mol % concentrated sulfuric acid were reacted for 6.5 hours at 150° C. as described in Example 2. A product having the following analysis was obtained after the removal by distillation of volatile constituents up to 135° C. in an oil pump vacuum (below 1 torr): epoxide oxygen content 0.20%, OH value 2.6, acid value 1.5, saponification value 237.6, iodine value 8.8.

Example 5

Vicinal Diacetyl Soybean Oil Fatty Acid Isooctyl Ester

6 Mol epoxidized soybean oil fatty acid isooctyl ester (epoxide oxygen content 4.99%), 12 mol acetic anhydride, 10 mol % acetic acid and 1 mol % concentrated sulfuric acid were reacted for 7.5 h with vigorous refluxing as described in Example 1. The reaction product was distilled in an oil pump vacuum (below 1 torr) up to 125° C. The dark brown residue, which could be bleached with hydrogen peroxide, hand the following analysis after the removal of precipitated salts by filtration: epoxide oxygen content 0.23%, saponification value 252.1, acid value 1.2, OH value 2.8, iodine value 20.4.

Example 6

Vicinal Dipropionyl Stearic Acid Isooctyl Ester

1 Mol of an epoxidized oleic acid isooctyl ester (epoxide oxygen content 3.228%) was stirred under reflux (approx. 150° C.) for 8 hours 2 mol propionic anhydride and 2.0 g concentrated sulfuric acid. The reaction mixture was neutralized with 7.4 g sodium methylate. The excess propionic anhydride was distilled off in vacuo at 15 torr. The distillation residue was distilled in vacuo up to 120° C. to remove volatile constituents. The distillation residue was freed from precipitated salts by filtration. A clear, dark brown liquid having the following analysis was obtained: epoxide oxygen content 0.30%, OH value 0.4, acid value 2.1, saponification value 235.3, iodine value 12.4.

I claim:

1. A process for the production of vicinally diacyloxy-substituted compounds from the group consisting of diacyloxyalkanes and esters of diacyloxy fatty acids with alkanols ad diacyloxy fatty alcohols and of esters of fatty acids with diacyloxy fatty alcohols of the formulae Ia, Ib, Ic and Id:

$$R^1[vic. (O-CO-R^2)_2]-H \qquad (Ia)$$

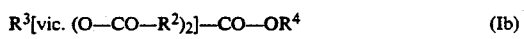

$$R^3[vic. (O-CO-R^2)_2]-CO-OR^4 \qquad (Ib)$$

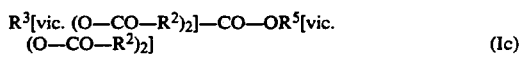

$$R^3[vic. (O-CO-R^2)_2]-CO-OR^5[vic. (O-CO-R^2)_2] \qquad (Ic)$$

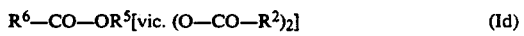

$$R^6-CO-OR^5[vic. (O-CO-R^2)_2] \qquad (Id)$$

in which
$R^1$ is a trivalent saturated $C_{6-22}$ hydrocarbon radical,
$R^2$ is a $C_{1-3}$ alkyl radical,
$R^3$ is a trivalent saturated $C_{10-21}$ hydrocarbon radical,
$R^4$ is a $C_{1-22}$ alkyl radical,
$R^5$ is a trivalent saturated $C_{16-22}$ hydrocarbon radical and
$R^6$ is a $C_{1-21}$ alkyl radical, by reaction of at least one epoxide compound of the formulae IIa, IIb, IIc and IId

$$R^7(EpO)-H \qquad (IIa)$$

$$R^8(EpO)-CO-OR^4 \qquad (IIb)$$

$$R^8(EpO)-CO-OR^9(EpO) \qquad \text{(IIc)}$$

$$R^6-CO-OR^9(EpO) \qquad \text{(IId)}$$

in which
$R^7(EpO)$ is an epoxidized $C_{6-22}$ alkenyl radical,
$R^8(EpO)$ is an epoxidized $C_{10-21}$ alkenyl radical and
$R^9(EpO)$ is an epoxidized $C_{16-22}$ alkenyl radical
and $R^4$ and $R^6$ are as defined above, with at least one $C_{2-4}$ carboxylic anhydride of the formula III $$(R^2-CO-)_2O \qquad \text{(III)}$$

in which $R^2$ is as defined above, at an elevated temperature, int eh presence of a catalytic quantity of a catalyst composition selected from the group consisting of a mixture of a carboxylic acid $R^2$—COOH, corresponding to the carboxylic anhydrides and a catalytic quantity of sulfuric acid or sulfuric acid.

2. A process as claimed in claim 1 wherein the reaction is carried out in the presence of a catalyst composition selected from the group consisting of a mixture of about 0.5 to about 15 mol % of the carboxylic acid corresponding to the carboxylic anhydride and about 0.1 to about 3 mol % sulfuric acid per mol epoxide functions present or about 0.1 to about 3 mol % sulfuric acid per mol of epoxide functions present.

3. A process as claimed in claim 1 wherein the reaction is carried out under ambient pressure at the boiling point of the reaction mixture.

4. A process as claimed in claim 1 wherein after the reaction, the reaction mixture is neutralized with an anhydrous base, unreacted $C_{2-4}$ carboxylic anhydride is removed by distillation and solid neutralization products are separated by filtration.

5. A process of claim 1 wherein the vicinal diacyloxy substituted compound is a compound of the formula $R^3(Vic(O-CO-R^2)_2)-CO-OR^4$ wherein $R^2$ is a $C_{1-3}$ alkyl radical, $R^3$ is a trivalent saturated $C_{10-21}$ hydrocarbon radical, and $R^4$ is a $C_{1-22}$ alkyl radical.

6. A process of claim 1 wherein the vicinally diacyloxy substituted compound is a compound of the formula $$R^3(vic.(O-CO-R^2)_2)-CO-OR^5(Vic.(O-C-OR^2)_2)$$

wherein $R^2$ is a $C_{1-3}$ alkyl radical, $R^3$ is a trivalent saturated $C_{10-21}$ hydrocarbon radical, and $R^5$ is a trivalent saturated $C_{16-22}$ hydrocarbon radical.

7. A process of claim 1 wherein the vicinally diacyloxy substituted compound is a compound of the formula $$R^6-CO-OR^5(Vic(O-CO-R^2)_2)$$

wherein
$R^2$ is a $C_{1-3}$ alkyl radical,
$R^5$ is a trivalent saturated $C_{16-22}$ hydrocarbon radical,
and $R^6$ is a $C_{1-21}$ alkyl radical.

* * * * *